US 9,658,136 B2

(12) United States Patent
Price

(10) Patent No.: US 9,658,136 B2
(45) Date of Patent: May 23, 2017

(54) MYCOTOXIN SAMPLE-COLLECTING KIT AND METHOD

(71) Applicant: Sue Price, Blairsville, GA (US)

(72) Inventor: Sue Price, Blairsville, GA (US)

( * ) Notice: Subject to any disclaimer, the term of this patent is extended or adjusted under 35 U.S.C. 154(b) by 249 days.

(21) Appl. No.: 14/594,982

(22) Filed: Jan. 12, 2015

(65) Prior Publication Data

US 2015/0301043 A1    Oct. 22, 2015

Related U.S. Application Data

(60) Provisional application No. 61/981,410, filed on Apr. 18, 2014.

(51) Int. Cl.
| | |
|---|---|
| *G01N 33/569* | (2006.01) |
| *G01N 1/04* | (2006.01) |
| *G01N 1/02* | (2006.01) |
| *G01N 1/00* | (2006.01) |

(52) U.S. Cl.
CPC .............. *G01N 1/04* (2013.01); *G01N 1/02* (2013.01); *G01N 2001/005* (2013.01); *G01N 2001/028* (2013.01)

(58) Field of Classification Search
CPC ...... G01N 1/02; G01N 1/04; G01N 2001/005; G01N 2001/028; G01N 33/56961
See application file for complete search history.

(56) References Cited

U.S. PATENT DOCUMENTS

| | | | |
|---|---|---|---|
| 2002/0136663 A1* | 9/2002 | Harris | G01N 1/28 422/400 |
| 2003/0045810 A1* | 3/2003 | Borkowski | A61B 10/0035 600/562 |
| 2005/0238535 A1* | 10/2005 | Knezevic | G01N 1/04 422/400 |
| 2007/0042355 A1* | 2/2007 | Adelson | G01N 33/569 435/5 |
| 2008/0014582 A1* | 1/2008 | Hooper | C12Q 1/6895 435/6.13 |

* cited by examiner

*Primary Examiner* — Francis Gray
(74) *Attorney, Agent, or Firm* — Clifford H. Kraft

(57) ABSTRACT

A mycotoxin sampling system including a kit and method using dry wipes that have been pre-tested on a lot basis to be clean from mycotoxins. Surfaces in an environment to be tested are wiped with a dry wipe over a particular area. The wipe is then sealed in a dry bag and sent to a laboratory for mycotoxin analysis. Results are returned by mail, email, or by telephone. The mycotoxin results are qualitative and quantitative. The kit contains all materials needed by an individual to perform mycotoxin tests and receive results. Advanced kits can contain testing reagents used to perform tests in the field in lieu of sending wipes to a laboratory.

5 Claims, 2 Drawing Sheets

FIG. 2

MYCOTOXIN SAMPLE-COLLECTING KIT AND METHOD

This application is related to, and claims priority from, U.S. Provisional Patent Application No. 61/981,410 filed Apr. 18, 2014. Application 61/981,410 is hereby incorporated by reference in its entirety.

BACKGROUND

Field of the Invention

The present invention relates generally to tests and test kits and more particularly to an environmental mycotoxin testing kit and method for commercial or individual use anywhere (usually in or around buildings) for testing of the environment for the presence and magnitude of mycotoxins.

Description of the Prior Art

According to Wikipedia, "a mycotoxin from the Greek for "fungus" and Latin for poison") is a toxic secondary metabolite produced by organisms of the fungi kingdom commonly known as molds. The term 'mycotoxin' is usually reserved for the toxic chemical products produced by fungi that readily colonize crops. One mold species may produce many different mycotoxins, and the same mycotoxin may be produced by several species."

"Mycotoxicosis is the term used for poisoning associated with exposures to mycotoxins. The symptoms of a mycotoxicosis depend on the type of mycotoxin; the concentration and length of exposure; as well as age, health, and sex of the exposed individual. The synergistic effects associated with several other factors such as genetics, diet, and interactions with other toxins have been poorly studied. Therefore it is possible that vitamin deficiency, caloric deprivation, alcohol abuse, and infectious disease status can all have compounded effects with mycotoxins. In turn, mycotoxins have the potential for both acute and chronic health effects via ingestion, skin contact, and inhalation. These toxins can enter the blood stream and lymphatic system, they inhibit protein synthesis, damage macrophage systems, inhibit particle clearance of the lung, and increase sensitivity to bacterial endotoxin." Numerous people become sick from Mycotoxins and do not know what they is causing the illness.

Mycotoxins can be detected from samples taken on-sight in buildings and homes. Prior art methods do not have a good way to easily environmentally test for mycotoxins. In the past methods cut out large pieces of drywall which is not at a good or convenient testing practice.

A Quote from the Book of Leviticus:

Cleansing from Defiling Molds

33 The Lord said to Moses and Aaron, 34 "When you enter the land of Canaan, which I am giving you as your possession, and I put a spreading mold in a house in that land, 35 the owner of the house must go and tell the priest, 'I have seen something that looks like a defiling mold in my house.' 36 The priest is to order the house to be emptied before he goes in to examine the mold, so that nothing in the house will be pronounced unclean. After this the priest is to go in and inspect the house. 37 He is to examine the mold on the walls, and if it has greenish or reddish depressions that appear to be deeper than the surface of the wall, 38 the priest shall go out the doorway of the house and close it up for seven days. 39 On the seventh day the priest shall return to inspect the house. If the mold has spread on the walls, 40 he is to order that the contaminated stones be torn out and thrown into an unclean place outside the town. 41 He must have all the inside walls of the house scraped and the material that is scraped off dumped into an unclean place outside the town. 42 Then they are to take other stones to replace these and take new clay and plaster the house. 43 "If the defiling mold reappears in the house after the stones have been torn out and the house scraped and plastered, 44 the priest is to go and examine it and, if the mold has spread in the house, it is a persistent defiling mold; the house is unclean. 45 It must be torn down—its stones, timbers and all the plaster—and taken out of the town to an unclean place."

Types of Mikotoxins

There are over 300 known Mycotoxins and probably many more to be discovered. *Stachybotrys chartarum*, a primary trichothecene producer is one of the major mycotoxins causing problems. Experts agree that ultimately, resolving the public health enigma of whether and how *Stachybotrys* inhalation evokes adverse health effects that contribute to DBRI will require state-of-the-art sampling/analytical methods to assess doses and timing of exposure to the fungus and its bioactive constituents as well as exploiting the use of relevant biomarkers."

Other Mycotoxins like trichothecenes (particularly inhaled ones) can cross the blood-brain barrier and can cause neurological damage at low level such as those found indoors in damp spaces. The U.S. Surgeon General and the Army say that mycotoxins are very potent and are effective biological warfare agents when used in concentration.

Mycotoxins are common in dust in any indoor environment that has had water damage. The sampling techniques used were a swab technique and a vacuum technique. What is needed is a contact wipe sampling technique, since that is more effective at collecting enough dust for statistically significant concentrations mycotoxin of dust for analysis.

Various literature and research has described the need for a better way to test for mycotoxins:

" . . . we tested the hypothesis that airborne trichothecene mycotoxins were present on particulates smaller than fungal conidia. This is important because in the indoor environment, fragments and other highly respirable particles greatly outnumber intact fungal conidia (17). Many widely used techniques such as bulk sampling (e.g., the adhesive tape technique, surface swabs, the collection of bulk materials, etc.) and viable/nonviable airborne conidium assessments (e.g., volumetric spore traps, Andersen impaction devices, etc.) are not designed for the collection and analysis of these potential health hazards. Previously, by using a controlled filtration setup (similar to the one depicted in Fig. □ FIG. 1), 1), we were able to demonstrate *S. chartarum* trichothecene mycotoxins on particles smaller than conidia (4). In the current study, we were able to show this same phenomenon after 24, 48, and 72 h of high-volume air sampling in a native mold-contaminated building. These findings indicate the need to collect this class of particles (in addition to larger particulate matter such as intact conidia) when conducting indoor air quality investigations.

Our study shows that macrocyclic trichothecene mycotoxins from *Stachybotrys chartarum* can become airborne in indoor environments contaminated with this organism. Our data suggest the need to test for these potential occupant health risks during indoor air quality investigations. Although we were able to semiquantitate airborne concentrations, it is still not known what levels of these mycotoxins pose a definitive human health risk. Furthermore, normal background levels (if they do exist) have not been characterized. Future research should focus on the relationship between respiratory exposure to airborne trichothecenes in fungus-contaminated buildings and human health issues resulting from such exposures. Additionally, alternative assays or means to measure airborne trichothecenes more accurately in such environments should be researched and developed.

"Ultimately, resolving the public health enigma of whether and how *Stachybotrys* inhalation evokes adverse health effects that contribute to DBRI will require state-of-the-art sampling/analytical methods to assess doses and timing of exposure to the fungus and its bioactive constituents as well as exploiting the use of relevant biomarkers."

Acknowledgments to 35 references.

Some of this work was supported by a grant from the Texas Higher Education Coordinating Board (010674-0006-2001) and by a Center of Excellence Award from Texas Tech University Health Sciences Center. Additional funding was provided by the UT-Houston School of Public Health Pilot Research Projects in Occupational Safety and Health. Articles from Applied and Environmental Microbiology.

As stated, there are approximately 300 known mycotoxins, the three being analyzed by the techniques are most significant from a public health standpoint. Aflatoxin is one of the most potent natural carcinogens. Ochratoxin is a suspected human carcinogen. Trichothecenes are highly potent as noted above.

It would be advantageous to have a kit and method that would allow easy collection of samples for mycotoxin testing using a sterile and mycotoxin-free wipe technique.

SUMMARY OF THE INVENTION

The present invention relates to a kit and method for testing an sampling for mycotoxins.

It is an object of the present invention to present a kit and method for making onsite environmental mycotoxin sampling easy and testing available at a reasonable price to anyone whom needs it. There is a great need for a mycotoxin sampling method that had not been addressed in the prior art, that could be 'built on' and or 'added to' as a base easily in the future, and that was specifically invented for capture of mycotoxins and fungal life-cycle components, including their produced residues, wastes, deposits and byproducts (which include mycotoxins).

An important component of the present invention is the onsite surface sampling system for mycotoxins, because without a good sample one cannot get a viable test result. The prior art method that was the standard for research and sampling in the field was taking of air samples. This was based on the almost "gaseous nature" of mycotoxins. The prior art fails because this method is not nearly as viable exactly because of the almost "gaseous nature' of mycotoxins' tiny size.

The present invention is based on, and takes into account, the fact that mycotoxins 'generally' fall because of gravity, are spread widely by factors including but not limited to air currents and/or are carried by other particles to settle, somewhat evenly into dust and other particles throughout an entire compartmented area or structure. The present invention presents a sampling method that includes wiping surfaces horizontally and/or vertically and gathering dust/residue/particles into the sample for the evidence of mycotoxin needed to create a viable sample.

The sampling system of the present invention includes a special wipe that can be called a 'Myco-Wipe™" as a new and simple sample collection tool never used before for mycotoxin capture. This is a special wipe that has been tested and certified to be mycotoxin free on a lot basis. Without such pre-sampling of lots for the presence of mycotoxins on the clean wipe, it is impossible to get reliable field results.

The complete Mycotoxin Environmental Testing Kit system of the present invention provides not only a sampling kit, but includes processing of the environmental mycotoxin samples taken, thereby generating mycotoxin test results. Using the mycotoxin capture process of the invention, the Onsite Surface Sampling System For Mycotoxin together with the new media collector, the MYCO-WIPE™, a viable mycotoxin sample is created. By using whole kit system, the end user is able to receive reliable test results otherwise not available. Now anyone can use the kit and systems easily to get something that was not available before in a way that was not available to them before.

Mycotoxin environmental test results, both qualitative and quantitative, are delivered by the present invention for the users informational purposes. Making their own samples by using the kit of the present invention developed especially for mycotoxins, users get both a qualitative and quantitative result of any mycotoxin contamination on building structure and other interior surfaces in a particular environment. The results are far superior to prior art air collection testing.

DESCRIPTION OF THE FIGURES

Several figures are presented to illustrate features of the present invention.

FIG. 2 shows a packaged mycotoxin kit.

Figure 1:
FIG. 1. shows sterile wipes and bags to hold them according to the present invention.

Several drawings and illustrations have been presented to aid in understanding the present invention. The scope of the present invention is not limited to what is shown in the figures.

DESCRIPTION OF THE INVENTION

The kit of the present invention includes sterile mycotoxin-collection media with wipes and/or swabs, wipes being preferred. Also included in the Kit is labeled media transport(s); such as Wipe transports and/or swab transports. These are mycotoxin-free bags that can be sealed for shipment to a lab.

Figure 2:
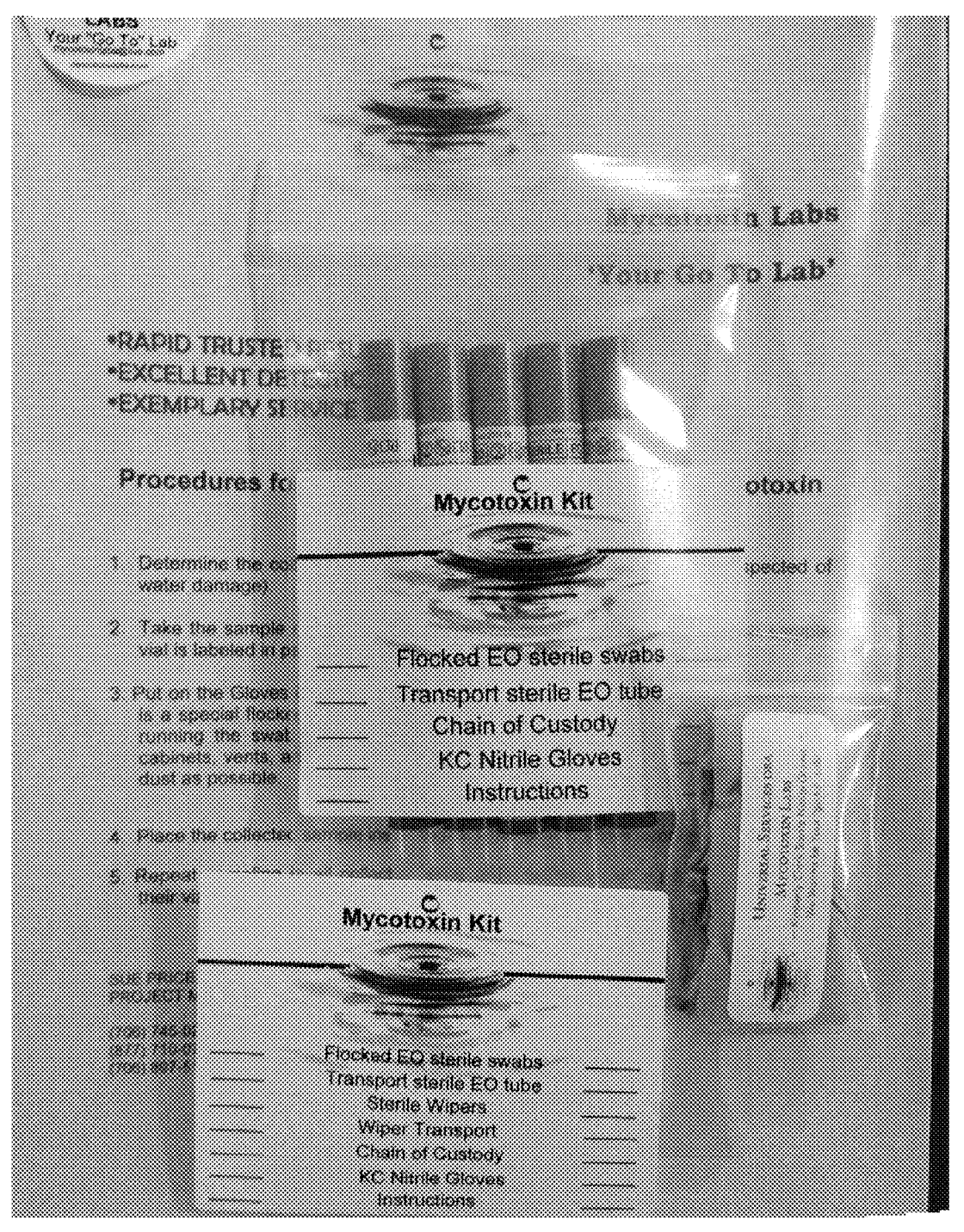

The kit can include gloves, instructions, paperwork and shipping materials and wipes. Swabs can be sterile swabs. Testing of the collected samples can be done by a certified laboratory, or the kit can contain testing reagents. FIGS. 1-2 show embodiments of such kits.

The wipe is superior to a swab for most surface area and collects a better sample with more on it then traditional methods or swabs. The wipes should preferably be mycotoxin clean as well as sterile. The preferred wipe is a sterile wipe such as Helapet™ available from CliniMed Co. of Bucks England. It is very important that samples of wipes be obtained in lots for kits and that a statistically significant number of samples of the wipes be taken from the lot, opened and tested for mycotoxins. This pre-testing assures that the clean wipes are not pre-contaminated with any mycotoxins. The wipes are used dry, not wet. This is important since if a wet wipe is used, it will pick up mold spores as well as other material. Then, when it is sealed in a carrier bag, new mold will grow in the wipe with the potential of creating new mycotoxins. This process can render the entire test invalid by producing false positives.

Because mycotoxins are very light solids, they fall due to gravity. They especially collect on horizontal surfaces. Therefore, a key wiping technique of the present invention is to horizontally wipe flat surfaces with the dry wipe. A preferred wipe area is around 10 sq. feet; however, this can vary with different environments. The second preferred place to wipe for mycotoxins is vertical surfaces such as walls, especially mold infested walls. Because the wipe is dry, and is sealed in the carrier, any mold picked up will not further grow.

The present invention supplies a kit and a method designed to reliably collect mycotoxin samples. As stated above, the samples are collected on mycotoxin-free dry wipers which are then analyzed for the presence and quantities of mycotoxins. The individuals' mycotoxin samples, are typically per directions in the kit, sent directly to a laboratory to be tested many times with pre-paid direct shipping envelope supplied in the kit. However, it is within the scope of the present invention to provide wipe testing methods and reagents as part of advanced kits. While this saves time, it will only be as reliable as the person performing the test. An accredited testing lab is the preferred method. The report and Certificate of Analysis are generally sent back to the person taking the sample along with an optional call by an expert to explain an individuals' results.

The present invention is an environmental mycotoxin testing kit that anyone can use, professional or a layperson. The present invention is easy to use and handle as well as light to transport and carry. The kit is strong, yet flexible enough to stay contemporary while always having the same function and a simple design that keeps in mind the ability to take advantage of more advanced test methods or better media as they are made available.

As other mycotoxins are discovered, the Kit's design and methods of collection can stay capable of collecting environmental material at any environmental site so that it may be tested for any mycotoxin that becomes detectable and can be quantitatively assessed.

The following are features of the kit and method of the present invention:

A. Mycotoxin Environmental Testing Kit
1. Sample collection media: wipes pre-tested on lot bases in sealed bags.
2. Labeled Transport(s)—bags that can be sealed for shipping.
3. Collection Gloves (for convenience and safety)
4. Instructions for shipping
5. Collection Procedure
6. Testing limitations and types—Alflatoxin, Ocratoxin, Tricothecene and other panels available
7. Pre-paid mailing envelope B. Chain of Custody
1. The environmental mycotoxin test kit user ID and personal data.
2. The location(s) of environmental mycotoxin sampling.
3. Who performed the environmental mycotoxin sampling.
4. The types of environmental mycotoxin tests to be completed.
5. Which unique wipe lot was used.
6. Handlers, including receiver.
7. Contacts for lab, project manager. Provision to get mycotoxin environmental test kit to user, sample to lab and results back, to user C. Results
2. Providing test result interpretation by expert if needed.
3. 5-day standard or 1-day rush.
4. Test results are communicated to user by email, phone, mail.

The following is a list of features of the present invention: Onsite Surface Sampling System for Mycotoxins and/or Fungal Life-Cycle Components and or their Residues, Deposits, By-Products For the capture of mycotoxins and/or fugal developmental components.
Sampling for mycotoxins in the environment.
Not food sampling.
Using natural or synthetic fibers to collect mycotoxins.
Offers superior mycotoxin collection on site.
By wiping surface(s) sampling for mycotoxins (not cleaning). primarily horizontal direction and/or vertical direction.
Capturing settled mycotoxins wherever they settle.
Not air sampling (where have to take in considerable amounts of air with extra equipment and that takes a longer time and the mycotoxins can be too small to be captured).
Using natural or synthetic fibers, sterile or non sterile and dry, to collect the settled mycotoxins on surfaces.
Sampling for mycotoxins by using means of primarily gravity is a better way to capture mycotoxin samples using their minuscule (almost gaseous) nature.
Mycotoxins have gravitational characteristics including primarily positive specific gravity with the characteristic of falling, and neutral specific gravity with the characteristic of floating, and negative specific gravity with the characteristic of rising. The present invention uses these facts that mycotoxins can take on any of these characteristics as they distribute into the environment, and the tendency for the mycotoxins to settle somewhat evenly on surfaces as carried by distribution factors present in the environment including but not limited to air currents, humidity and/or initial discharge momentum.
Using the process of gathering mycotoxins mingling and or adhesion to particulates present in environment including but not limited to dust, hair, skin, other particles, all surfaces.
Using the process of fungal development life cycle processes which can produce bio-chemical components including their produced bio-chemically active or inactive residues, deposits, byproducts, wastes (which include all mycotoxins). Some which can form continually, some which are formed intermittently in varying amounts.

The mycotoxin sampling system of the present invention can stand alone or can also
be used in conjunction with the following:
Mycotoxin sample processing system may be onsite or off.
Detection mechanism system may be onsite or off.
Test result distribution system may be onsite or off.

Several descriptions and illustrations have been presented that aid in understanding the present invention. One with skill in the art will realize that numerous changes may be made without departing from the spirit of the invention. Each of these changes and variations is within the scope of the present invention.

I claim:
1. A mycotoxin test method comprising:
obtaining or creating a plurality of lots of dry wipes;
sampling each lot randomly to determine that the lot is mycotoxin-free;

instructing a user to dry wipe a surface at a particular location with a single wipe from one of said lots;

instructing the user to seal the used wipe in a carrier container and to seal the carrier container;

instructing the user to supply a carrier container ID with the carrier container identifying said location;

instructing the user to send the carrier container and carrier container ID to a laboratory for qualitative and quantitative analysis for mycotoxins.

2. The method of claim 1 wherein the dry wipes are a natural or synthetic cloth.

3. The method of claim 1 wherein samples of dry wipes from said lot are supplied in a sealed, sterile bag.

4. The method of claim 1 wherein said carrier container ID is supplied attached to a carrier container.

5. A kit for mycotoxin testing that includes:

at least one dry wipe from a lot randomly tested for absence of mycotoxins supplied in a sealed bag;

at least one carrier container adapted to be sealed for holding the dry wipe after sampling;

a set of ID information for the test;

at least one shipping label to ship the carrier and the ID information to a remote testing laboratory;

a set of instructions explaining the mycotoxin test method including:

an instruction to remove the dry wipe from the sealed bag;

an instruction to dry wipe an approximate predetermined surface area in an environment with the wipe;

an instruction to seal the dry wipe in the carrier;

an instruction to send the carrier to the testing laboratory for qualitative and quantitative mycotoxin analysis.

* * * * *